United States Patent
Biedermann et al.

(10) Patent No.: US 6,200,348 B1
(45) Date of Patent: Mar. 13, 2001

(54) SPACER WITH ADJUSTABLE AXIAL LENGTH

(75) Inventors: Lutz Biedermann, Villingen; Jürgen Harms, Waldbronn, both of (DE)

(73) Assignee: Biedermann, Motech GmbH, Schwenningen (DE)

(*) Notice: Subject to any disclaimer, the term of this patent is extended or adjusted under 35 U.S.C. 154(b) by 0 days.

(21) Appl. No.: 09/402,425

(22) PCT Filed: Jan. 27, 1999

(86) PCT No.: PCT/EP99/00526

§ 371 Date: Oct. 4, 1999

§ 102(e) Date: Oct. 4, 1999

(87) PCT Pub. No.: WO99/39665

PCT Pub. Date: Aug. 12, 1999

(30) Foreign Application Priority Data

Feb. 6, 1998 (DE) .............................................. 198 04 765

(51) Int. Cl.⁷ .............................. A61F 2/44; A61B 17/56
(52) U.S. Cl. .................................... 623/17.11; 623/17.16; 606/61
(58) Field of Search .................................. 606/60, 61, 69, 606/72, 73, 90; 623/17.11, 17.16

(56) References Cited

U.S. PATENT DOCUMENTS

| 4,553,273 | * | 11/1985 | Wu ........................................ 623/18 |
| 4,599,086 | | 7/1986 | Doty ....................................... 623/17 |
| 4,892,546 | | 1/1990 | Kotz et al. ............................. 623/18 |
| 5,569,263 | | 10/1996 | Hein ..................................... 606/102 |
| 5,571,192 | * | 11/1996 | Schonhoffer .......................... 623/17 |
| 5,702,453 | * | 12/1997 | Rabbe et al. .......................... 623/17 |
| 5,702,455 | | 12/1997 | Saggar .................................. 623/17 |
| 5,776,197 | * | 7/1998 | Rabbe et al. .......................... 623/17 |
| 5,776,198 | * | 7/1998 | Rabbe et al. .......................... 623/17 |
| 5,916,267 | * | 6/1999 | Tienboon .............................. 623/17 |
| 5,980,522 | * | 11/1999 | Koros et al. .......................... 606/61 |
| 5,989,290 | * | 11/1999 | Biedermann et al. ................ 623/17 |
| 6,039,762 | * | 3/2000 | McKay .................................. 623/17 |

FOREIGN PATENT DOCUMENTS

| 80 16 889 U1 | 9/1980 | (DE) . |
| 195 19 101 A1 | 11/1996 | (DE) . |
| 196 22 827 A1 | 12/1997 | (DE) . |
| 296 16 778 U1 | 3/1998 | (DE) . |
| 0 290 767 | 11/1988 | (EP) . |
| 0 490 159 | 6/1992 | (EP) . |
| 0 832 622 A2 | 4/1998 | (EP) . |
| WO 92/01428 | 2/1992 | (WO) . |

* cited by examiner

Primary Examiner—Paul J. Hirsch
Assistant Examiner—Michael B. Priddy
(74) Attorney, Agent, or Firm—George W. Neuner, Esq.

(57) ABSTRACT

A spacer for insertion between two vertebrae has a variable axial length. The spacer comprises a first sleeve-shaped shape member 1 and a second member 2 which is slidably guided within the first member in axial direction relative thereto for adjusting the overall length. The second member 2 comprises, on its outer portion facing the first member 1, an axially extending portion having ratchet notch means 18, and the first member 1 has an engagement member 23 cooperating with the ratchet notch means 18 for displacement to a desired overall length.

13 Claims, 2 Drawing Sheets

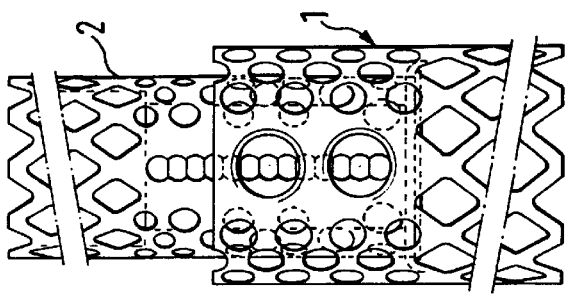
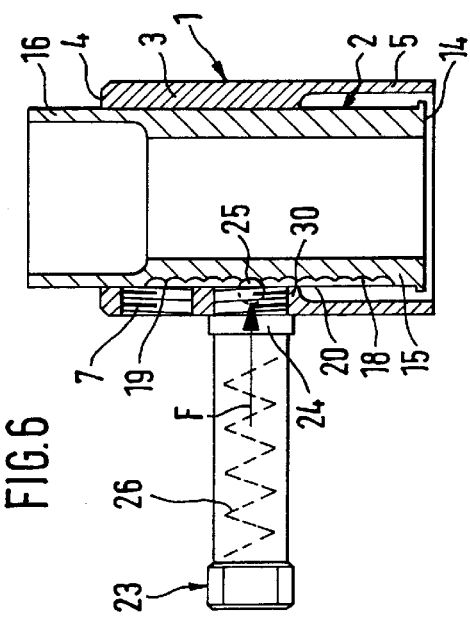
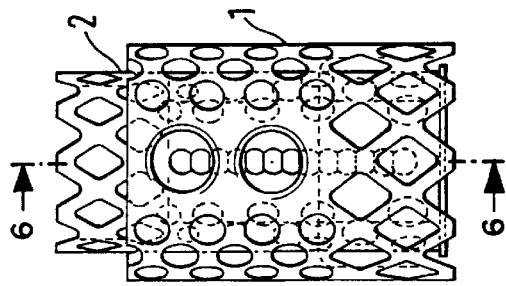
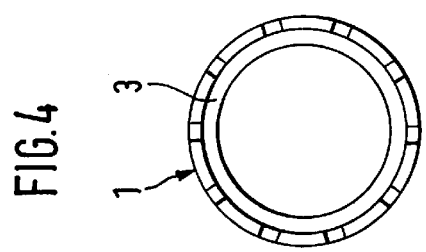
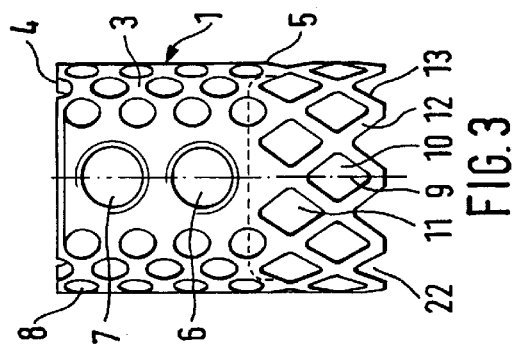
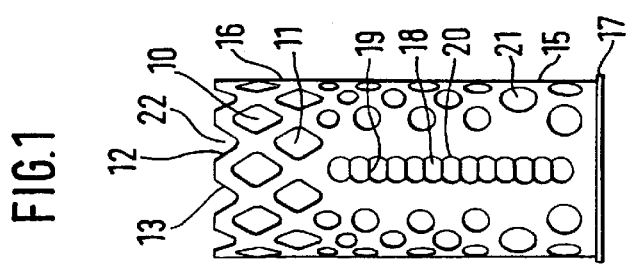
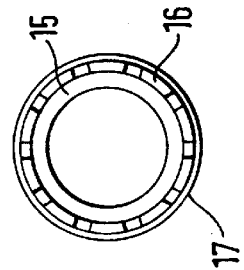

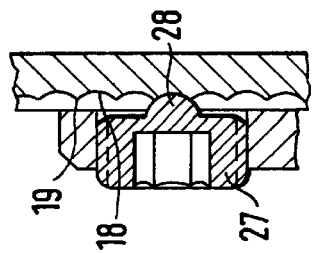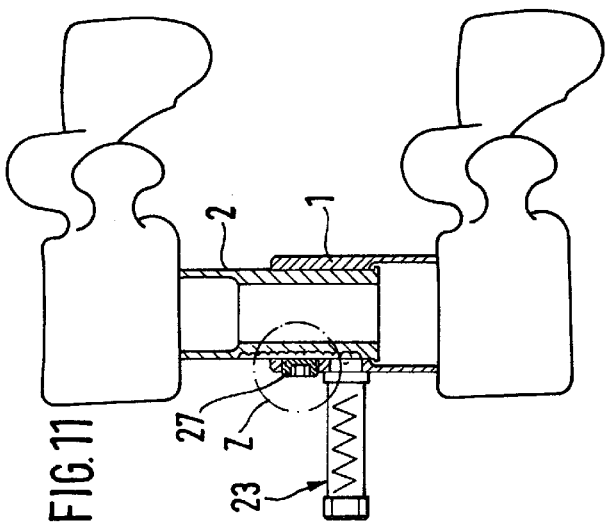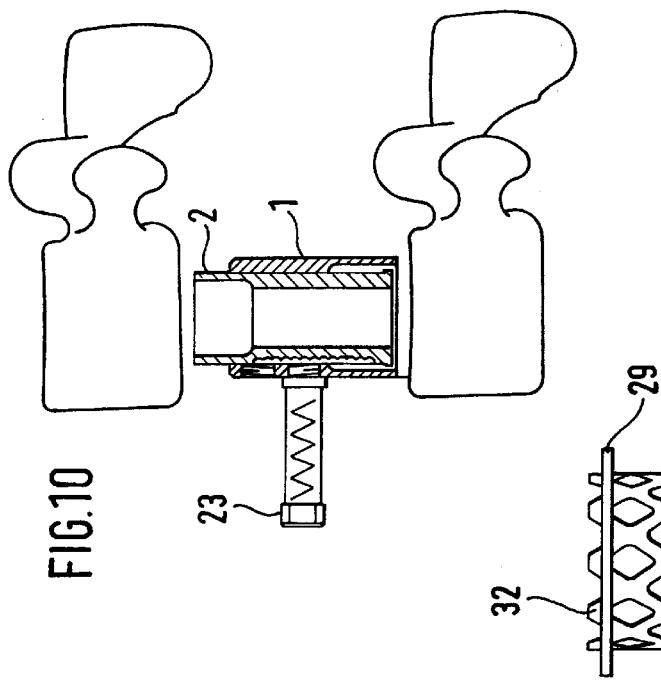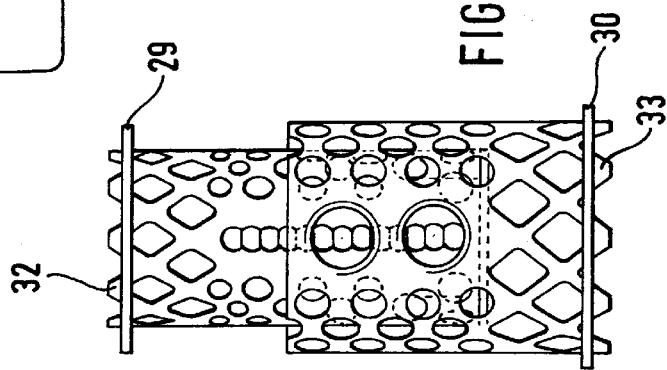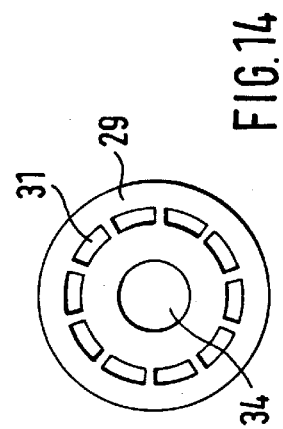

SPACER WITH ADJUSTABLE AXIAL LENGTH

The invention relates to a spacer for insertion in particular between two vertebrae, the spacer having an adjustable axial length, a sleeve-like first member and a second member which is guided within the first member and displaceable in axial direction relative to the first member for adjustment of the overall length.

A spacer of this type is known from DE 196 22 827 A1. The second member guided within the first member comprises a thread on its surface and a stop ring threaded onto the thread. The first member is put onto the second member and both members are pushed into each other up to the stop formed by the screwed-on ring. After insertion between the two vertebrae the final length is adjusted by screwing the ring towards the first sleeve for extending the spacer. In the final position both members are fastened relative to each other using a fastening screw. Both free ends of the spacer are provided with end plates with faces having blades for cutting into the adjacent vertebra. The requirement of rotating the stop ring around the longitudinal axis results in a certain torque exerted on both members which causes the risk that the blades at the free ends of the members injure the adjacent vertebrae by exertion of the torque when inserting the spacer. Rotation is very difficult because of the limited space available for operation.

It is the object of the invention to provide a spacer of the initially described kind which requires no rotational force or movement for adjusting its length so that the draw-backs of the prior art are avoided.

Using a ratchet the surgeon inserting the spacer may move back and forth between different, apparently ideal positions before finally locking the spacer in its ideal length.

The form of the corresponding edge portions of the spacer members, has the advantage that the surgeon may angularly adjust the end faces of this variable spacer.

Further features and advantages of the invention will be apparent from the description of an embodiment with reference to the Figures. In the Figures:

FIG. 1 is a side view of one member of the spacer;
FIG. 2 is a top view of the member shown in FIG. 1;
FIG. 3 is a side view of the other member of the spacer;
FIG. 4 is a bottom view of the member shown in FIG. 3;
FIG. 5 is a side view of both members after insertion into one another;
FIG. 6 is a sectional view along line A—A in FIG. 5 with inserted tool;
FIG. 7 is a side view of a locking screw;
FIG. 8 is a top view of the locking screw;
FIG. 9 is a side view of the spacer with angularly adjusted free ends;
FIG. 10 shows the spacer with tool inserted between two vertebrae;
FIG. 11 shows the spacer with locking screw adjusted to the correct length;
FIG. 12 is an enlarged representation of the inserted locking screw;
FIG. 13 shows the spacer with end plates in position; and
FIG. 14 is a top view of one of the end plates.

As best shown in the FIGS. 5 and 6 the spacer comprises an outer sleeve 1 forming a first member and an inner sleeve 2 forming a second member.

As best shown in the FIGS. 3, 4 and 6 the outer sleeve 1 has a first jacket portion 3 extending from the first free end 4 towards its other free end by more than half of the sleeve length. This jacket portion has a first inner diameter. At the following second jacket portion 5 the jacket wall is thinned on its inner side and has a second inner diameter which is greater than the first inner diameter. As best shown in FIG. 3 the first jacket portion comprises two threaded bores 6 and 7 positioned one above the other in axial direction of the sleeve. Moreover, the first jacket portion has a plurality of apertures 8 which are distributed across the entire jacket portion and formed as bores extending through the jacket. The second jacket portion 5 has diamond-shaped apertures 10, 11 with the longitudinal diagonal thereof extending parallel to the sleeve axis 9 in the manner shown in FIG. 3. A first group of such diamond-shaped apertures 10 extends in circumferential direction adjacent to the edge and this first group is followed, in direction towards the first free end 4, by a second group 11 of the diamond-shaped apertures, whereby the second group is offset from the first group by half a diamond height in axial direction. This produces a net of crossing web-shaped strips 12, 13 including an acute angle therebetween and equal angles with the longitudinal diagonal of the diamonds. The diamonds and the strips defining the same are sized to always obtain an integer number of diamonds in circumferential direction. The edge thus formed comprises prongs formed by the web-shaped strips and indentations 22 therebetween.

As best shown in the FIGS. 1, 2 and 6 the second member comprises a first shell portion 15 having a first outer diameter adjacent to the first free end 14 of the first shell portion. In the embodiment shown the first shell portion extends over slightly more than two thirds of the axial length and is followed by a second shell portion 16 having the same outer diameter and extending up to the second free end. The outer diameter is chosen to allow a sliding guidance of the inner sleeve in the first jacket portion 3 of the outer sleeve in the manner best shown in FIG. 6. The first free end 14 of the inner sleeve is provided with a collar 17 having a diameter which is greater than the diameter of the first shell portion and of the first inner diameter of the outer sleeve and which is smaller than the inner diameter of the second jacket portion 5 of the outer sleeve.

The first shell portion 15 comprises a plurality of spherical segment-shaped recesses 18 formed side by side in a direction parallel to the sleeve axis 9 and having a depth less than the radius thereof. As best shown in FIG. 1 the spacing or pitch of two adjacent recesses is less than the diameter of the edge defining the spherical segment-shaped recesses. As a consequence the boundary line 19 between two adjacent recesses is lower than the edge 20 proper of the recesses. The region of the recesses 18 extends along almost the entire length of the first shell portion 15. Apertures 21 formed as bores extending through the sleeve are provided in the first shell portion over the entire surface thereof, in a manner corresponding to the apertures 8. The second shell portion 16 is formed in a manner corresponding to the second jacket portion 5 of the first sleeve and comprises correspondingly arranged diamond-shaped apertures 10, 11 with strips 12, 13 therebetween. At the free end of the sleeve the strips converge towards each other and define respective indentations 22 with projecting, relatively sharp prongs therebetween.

For assembling the spacer the inner sleeve 2 is pushed into the outer sleeve 1 from the side of its second jacket portion 5 in the manner best shown in the FIGS. 5 and 6. The maximum pushing depth is defined by the collar 17 coming into contact with the inner shoulder formed between the two jacket portions 3 and 5.

A tool 23 is provided for enabling the spacer to be inserted between the two adjacent vertebrae and to be expanded to the desired length and locked in the manner best shown in the FIGS. 10 and 11. The tool 23 has an external thread provided at one end thereof and fitting the internal thread of the two threaded bores 6, 7. The external thread is followed by a shoulder 24 forming a stop when screwing the tool into the threaded bore 6 or 7. A ball 25 is mounted at the face of the tool adjacent to the external thread and resiliently biased outwardly in direction of the arrow F by a schematically indicated internal spring. The diameter of the ball is equal to or slightly less than the diameter of the spherical recesses 18 so that the ball exactly fits the spherical segment-shaped portions. In this assembly state of the spacer both sleeves can be displaced relative to each other and extended to a maximum length as best shown in the FIGS. 5 and 9. The spring-biased ball 25 cooperates with the spherical segment-shaped recesses 18 in the manner of a ratchet whereby the extension can be varied by the spacing of two recesses or a multiple thereof. The two sleeves are extended during the operation by applying a suitable spreading tool.

Locking screws 27 shown in the FIGS. 7 and 8 have an outer diameter sized to cooperate with the threaded bores 6, 7. As best shown in the FIGS. 7 and 12 a spherical segment 28 is provided in the center of an end face of the locking screw. The dimensions of the spherical segment 28 correspond to those of the spherical segment freely projecting from the end face of the tool 23. The opposite end face has a hexagon bore for engagement of a screw driver.

In operation the spacer inserted according to FIG. 10 is first adjusted to its optimum length shown in FIG. 11 and held by the tool 23. Thereafter a locking screw 27, as shown in FIG. 12, is firmly screwed into the second threaded bore to finally lock the two sleeves in position relative to each other. After unscrewing the tool 23 a corresponding screw 27 is inserted into the second threaded bore to provide an additional lock.

As shown in FIG. 9 the portions 5 and 16 having the diamond-shaped apertures offer the possibility to adjust the angular inclination of the edge portions engaging the vertebrae using a suitable cutting tool and to form at the same time indentations and prongs at the edge for engaging the adjacent vertebrae.

As shown in the FIGS. 13 and 14 end plates 29 and 30 have holes 31 for putting the end plates onto the projecting prongs 32, 33 and apertures 34 to enhance ingrowing.

In the above-described embodiment the two sleeves are formed as cylinders. However, they may have other cross-sectional shapes, the cross-sectional shape being defined by the parts to be connected.

What is claimed is:

1. A spacer for insertion between two vertebrae, said spacer having a variable axial length and comprising a sleeve-shaped first member and a second member guided within the first member to be slidable relative thereto in an axial direction thereof for adjusting an overall length, wherein the second member comprises an outer wall and ratchet notches provided at its outer wall facing the first member and extending in the axial direction, and wherein the first member comprises a wall having an engagement member, which cooperates with the ratchet notches for adjusting a desired overall length of the spacer.

2. A spacer according to claim 1, wherein the engagement member is inserted into the wall of the first member and has a spring-biased ratchet member, and the spacer member further comprises a locking member that cooperates with the ratchet notches for locking both the first and second members at the desired overall length.

3. A spacer according to claim 2, wherein the ratchet notches comprise a plurality of axially spaced recesses, and wherein the ratchet member comprises a spring-biased ball.

4. A spacer according to claim 3, wherein the recesses comprise hollow, spherical segments.

5. A spacer according to claim 4, wherein a pitch of the centers of two adjacent recesses is less than the ball diameter.

6. A spacer according to claim 4, wherein a pitch of the centers of two adjacent recesses is less than the diameter of the peripheral edge of the recess.

7. A spacer according to any one of the claims 2 to 6, wherein the locking member comprises a screw having an end face facing the ratchet notches and a spherical segment, which is provided on the end face of the screw and is dimensioned to exactly fit a recess.

8. A spacer according to any one of the claims 2 to 6, wherein the first member comprises a first threaded bore for receiving the engagement member and a second threaded bore disposed above or below the first threaded bore and in a direction of a center axis for receiving the locking member.

9. A spacer according to any of the claim 7, wherein the first member comprises a first threaded bore for receiving the engagement member and a second threaded bore disposed above or below the first threaded bore and in a direction of a center axis for receiving the locking member.

10. A spacer according to any one of the claims 2 to 6, wherein the first and second members have free ends that are serrated.

11. A spacer according to any one of the claim 2 to 6, wherein the walls of both first and second members comprise a plurality of apertures formed such that a plurality of said apertures around a circumferential direction at least partially coincide in each ratchet position.

12. A spacer according to claim 10, wherein the walls of both first and second members comprise a plurality of apertures formed such that a plurality of said apertures around a circumferential direction at least partially coincide in each ratchet position.

13. A spacer according to any one of the claims 2 to 6, wherein a stop is provided for limiting a relative displacement to provide a maximum overall length of the spacer.

* * * * *